(12) United States Patent
Passlick-Deetjen et al.

(10) Patent No.: US 8,915,875 B2
(45) Date of Patent: Dec. 23, 2014

(54) ADSORBENTS FOR THE ADSORPTION OF HEPCIDIN

(75) Inventors: Jutta Passlick-Deetjen, Giessen (DE); Wolfgang Hofmann, Frankfurt (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 154 days.

(21) Appl. No.: 13/321,329

(22) PCT Filed: Jul. 15, 2010

(86) PCT No.: PCT/EP2010/004303
§ 371 (c)(1), (2), (4) Date: Nov. 18, 2011

(87) PCT Pub. No.: WO2011/009555
PCT Pub. Date: Jan. 27, 2011

(65) Prior Publication Data
US 2012/0063954 A1 Mar. 15, 2012

(30) Foreign Application Priority Data

Jul. 20, 2009 (DE) .......................... 10 2009 034 150

(51) Int. Cl.
| | |
|---|---|
| *A61M 37/00* | (2006.01) |
| *A61M 1/00* | (2006.01) |
| *G01N 33/74* | (2006.01) |
| *A61M 1/36* | (2006.01) |
| *B01J 20/32* | (2006.01) |

(52) U.S. Cl.
CPC .............. *G01N 33/74* (2013.01); *A61M 1/3679* (2013.01); *B01J 20/3248* (2013.01); *B01J 20/3274* (2013.01)
USPC ........................ 604/5.01; 422/44; 530/391.1

(58) Field of Classification Search
CPC ....... A61M 1/16; A61M 1/34; A61M 1/3679; A61M 2202/0057; A61M 2202/0421
USPC ........ 604/4.01–6.16; 210/645–646, 767, 679, 210/635, 660, 691, 905; 128/898; 502/400–402; 521/400–402, 30–31, 521/25, 73, 75; 525/54.1; 428/402; 530/391.1

See application file for complete search history.

(56) References Cited

U.S. PATENT DOCUMENTS

| | | | |
|---|---|---|---|
| 5,476,715 A | 12/1995 | Otto | |
| 6,416,487 B1 * | 7/2002 | Braverman et al. | .......... 604/5.01 |

(Continued)

FOREIGN PATENT DOCUMENTS

| | | |
|---|---|---|
| CN | 1346280 | 4/2002 |
| CN | 1408442 | 4/2003 |

(Continued)

OTHER PUBLICATIONS

Peslova, G. "Hepcidin, the hormone of iron metabolism, is bound specifically to alpha-2-macroglobulin in blood." Blood. 2009 Jun. 11;113(24):6225-36.*

(Continued)

*Primary Examiner* — Philip R Wiest
(74) *Attorney, Agent, or Firm* — Jacobson Holman Hershkovitz, PLLC.

(57) ABSTRACT

The invention relates to a device and a method for depletion of hepcidin from blood for treatment of iron deficiency, in particular in anemic patients suffering from chronic renal failure, with the goal of increasing the availability of iron in the body and thus improving the treatment of the anemia. The hepcidin adsorbent comprises a matrix and a hepcidin-binding ligand covalently bonded to the matrix with an affinity having a dissociation constant KD of less than 200 nM.

6 Claims, 1 Drawing Sheet

(56) References Cited

U.S. PATENT DOCUMENTS

Figure 1:
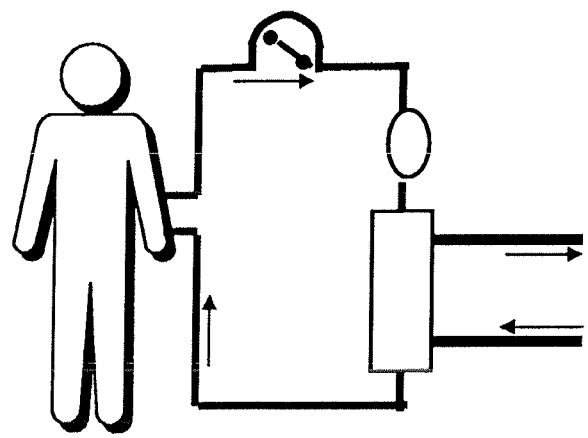

| | | | | |
|---|---|---|---|---|
| 7,846,121 | B2 * | 12/2010 | Wuepper | 604/4.01 |
| 2008/0213277 | A1 * | 9/2008 | Sasu et al. | 424/141.1 |
| 2008/0255344 | A1 | 10/2008 | Heinrich | |
| 2009/0136495 | A1 * | 5/2009 | Gately et al. | 424/133.1 |

FOREIGN PATENT DOCUMENTS

| | | |
|---|---|---|
| CN | 1572332 | 2/2005 |
| CN | 1612746 | 5/2005 |
| CN | 101279242 | 10/2008 |
| EP | 0 424 698 A1 | 5/1991 |
| EP | 1 481 700 | 12/2004 |
| WO | WO 03/090924 | 11/2003 |
| WO | WO 2006/042507 | 4/2006 |
| WO | WO 2008/097461 | 8/2008 |
| WO | WO 2009/044284 | 4/2009 |
| WO | WO 2009/058797 | 5/2009 |

OTHER PUBLICATIONS

Peslova Gabriela et al; "Hepidin, the Hormone of Iron Metabolism, is Bound Specifically to Alpha-2-macroglobulin in Blood", BLOOD, vl. 113, No. 24, Jun. 2009, pp. 6225-6236.

* cited by examiner

ADSORBENTS FOR THE ADSORPTION OF HEPCIDIN

This is a national stage of PCT/EP10/004303 filed Jul. 15, 2010 and published in German, which claims the priority of German number 10 2009 034 150.1 filed Jul. 20, 2009, hereby incorporated by reference.

The invention relates to a device and a method for lowering the blood hepcidin levels for treatment of iron deficiency, in particular of anemic patients suffering from chronic renal disease, with the goal of increasing the availability of iron in the body and thus improving the treatment of pre-existing anemia.

Human hepcidin is coded as a prepropeptide with 84 amino acids. Of these, 24 N-terminal amino acids code for a signal sequence directed at the endoplasmic reticulum, 35 amino acids forming the proregion and the 25 C-terminal amino acids forming the actual bioactive sequence.

The C-terminal region, also called hepcidin-25, hormonally regulates the body's iron balance. N-Terminal degradation products of hepcidin-25, in particular hepcidin-20, which has 20 amino acids, and hepcidin-22, which has 22 amino acids, are also frequently found in the body. Mutations in the hepcidin gene are associated with severe juvenile hemochromatosis, overloading of cells with iron. In contrast with that, hepcidin may be overexpressed in the presence of inflammatory stimuli. The stimulation is triggered by secretion of inflammatory interleukin IL-6. Therefore, a strong correlation can be observed between iron deficiency anemia, hepcidin expression and chronic inflammation, such as that with chronic kidney disease (CKD) in particular.

Hepcidin inhibits the release of iron by the cells by degrading ferroportin, the iron export protein. Iron is removed from the cell into the plasma by ferroportin. In a healthy body, the absence of hepcidin therefore results in increased elimination of iron from the cells and overloaded iron levels in the blood plasma. In patients with chronic inflammation and elevated hepcidin levels, there is an accumulation of iron in the cells, leading to a deficiency of transferrin-bound iron in the blood plasma. In patients with chronic renal failure, this effect is further exacerbated by inadequate elimination of hepcidin from the blood level via the kidneys. If the level of iron in the blood plasma is too low, this is associated with the disease presentation of anemia, because an adequate iron supply must be ensured for effective erythropoiesis, i.e., the production of red blood cells. A lack of a suitable supply of iron to the blood plasma is thus not only a possible cause of anemia per se but also inhibits successful treatment of anemia by medication, e.g., with EPO.

Patients suffering from chronic renal failure therefore have an especially high incidence of iron deficiency anemia because secretion of hepcidin is elevated due to the constant inflammatory state, but effective hepcidin elimination is additionally impaired because of the renal failure.

WO 2009/058797, WO 08/097,461 and WO 2009/044284 describe a hepcidin-binding antibody and the treatment of anemic patients by systemic medicinal administration of the antibody. A systemic antibody therapy, in addition to the typical adverse effects such as fever, chills, itching, sweating, a drop in blood pressure, a tendency to infections, water retention, often triggered by a secondary immune response to the antibody itself, additionally puts the body in an inflammatory state, which promotes the production of hepcidin, as described above.

The object of the present patent is to provide means and methods for lowering the hepcidin level in the blood plasma while avoiding the disadvantages of medicinal antibody therapy.

This object is achieved according to the invention by the independent claims. Partial objects are advantageously achieved by the dependent claims.

Within the scope of the invention, hepcidin is decreased by adsorption of hepcidin in an extracorporeal circulation. To do so, blood is withdrawn continuously from the patient, the blood thus withdrawn is sent through an adsorbent, which binds hepcidin, and the hepcidin-depleted blood is returned to the patient. For this purpose, a device is made available according to the invention, permitting an extracorporeal circulation and containing a depletion unit for depletion of hepcidin. The depletion unit consists of a housing and an adsorbent contained therein to specifically bind hepcidin. The inventive adsorbent consists of a solid-phase matrix to which a specifically hepcidin-binding ligand is covalently bonded.

The invention is described below with reference to the accompanying drawings as examples, in which:

FIG. 1 shows a schematic block diagram of a preferred embodiment of an inventive device having a first line device 10, a second line device 12, a depletion unit 14 and a body fluid delivery device 16 plus optionally a hemodialyzer 30.

Figure 2:
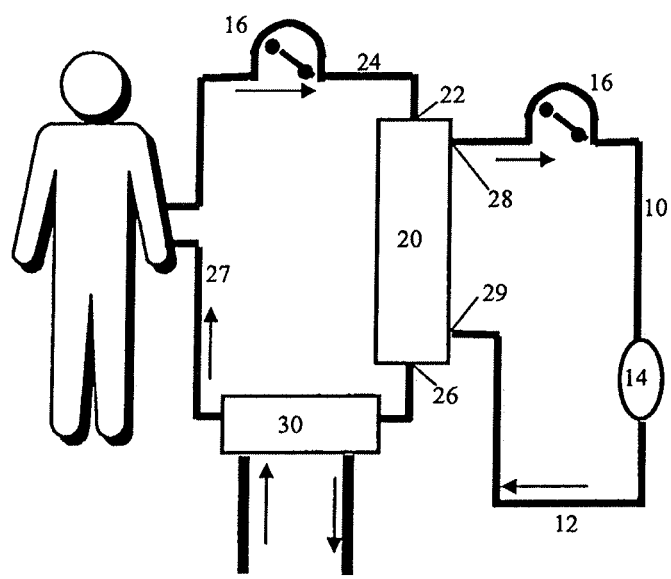

FIG. 2 shows a schematic block diagram of another preferred embodiment of an inventive device having a first line device 10, a second line device 12, a depletion unit 14, a fluid delivery device 16, a plasma filter 20, a third line device 24, a fourth line device 27, a fluid supply inlet 22 on the unfiltered side, a fluid removal outlet 26 of the unfiltered side, a fluid removal outlet 28 of the filtered side, a fluid supply inlet 29 of the filtered side and optionally a hemodialyzer 30.

According to the present invention, a possible medical device for establishing an extracorporeal circulation for depletion of hepcidin from whole blood therefore includes a first line device (10) and a second line device (12), which can be connected to the patient (P), a depletion unit located between the first line device (10) and the second line device (12) and connected thereto by a fluid-tight seal, this depletion unit (14) containing an adsorbent according to claim 1 and at least one controllable body fluid delivery device (16), which is located in the first line device (10) and/or second line device (12), wherein a controllable flow of body fluid through the line devices (10, 12) and the depletion unit (14) can be created by means of the at least one body fluid delivery devices (16), such that the first line device (10) is designed to continuously supply the body fluid withdrawn from the patient (P) to the depletion unit (14) and the second line device (12) is designed to continuously supply the body fluid to the patient (P).

Iron deficiency occurs with an especially high incidence in patients with chronic renal failure. These patients are often treated by hemodialysis as a substitute for renal activity. An extracorporeal circulation is likewise established in hemodialysis, wherein blood is drawn continuously from the patient and passed through a semipermeable membrane to thereby remove toxic substances and fluid from the blood by dialysis on the membrane, the purified blood being returned to the patient. Within the scope of the present invention, it is therefore advantageous to combine the two treatments by combining both a hemodialyzer and a hepcidin depletion unit in the medical device that serves to establish the extracorporeal circulation. Hepcidin depletion by adsorption can be accomplished simultaneously with hemodialysis in this way.

It is known that adsorption of substances from blood plasma is often more effective than adsorption from whole blood. An alternative inventive device therefore separates blood into cell-free blood plasma and a cell suspension via a secondary circulation. Hepcidin is then adsorbed from blood plasma by the depletion unit in the secondary circulation. The depleted blood plasma is immediately returned from the secondary circulation back to the primary circulation.

A corresponding medical device also comprises, in addition to the medical device described above, a plasma filter (20) with an unfiltered side and a filtered side, the unfiltered side being separated from the filtered side by at least one filter material, wherein a fluid supply inlet (22) of the unfiltered side is connected to a third line device (24), which can be connected to the patient, a fluid removal outlet (26) of the unfiltered side is connected to a fourth line device (27) which can be connected to the patient, a fluid removal outlet (28) of the filtered side is connected to the first line device (10), and a fluid supply inlet (29) of the filtered side is connected to the second line device (12).

The filter material of the plasma filter is advantageously designed so that blood cells remain in the primary circulation, whereas macromolecules are able to pass through the plasma filter. The cutoff of the plasma filter is therefore preferably between 1000 and 5000 kDa.

Hepcidin is found primarily in bound form in blood or blood plasma. Hepcidin binds with a high affinity to alpha-2-macroglobulin with a dissociation constant of 177 nM. Physiologically active hepcidin-25 and its fragments have a molecular weight of less than 3 kDa. Nevertheless, hepcidin is eliminated only inadequately in hemodialysis by binding to alpha-2-macroglobulin (750 kDa), which cannot pass through the dialysis membrane. To ensure effective adsorption of hepcidin from blood or blood plasma, the affinity for the adsorbent used in the depletion unit must be at least of the same order of magnitude as the affinity of hepcidin for alpha-2-macroglobulin. This is achieved by an adsorbent with ligands bound to the solid phase having an affinity for hepcidin-25 with a dissociation constant of less than 200 nM. The dissociation constant is preferably less than 50 nM, more preferably less than 5 nM and especially preferably less than 1 nM.

Hepcidin-binding ligands in the sense of the present invention may be monoclonal antibodies and their fragments. Alternative ligands in the sense of the invention may be hepcidin-binding peptides. Such peptides may be derived from the hepcidin-binding peptide sequence of alpha-2-macroglobulin. Suitable ligands in the sense of the invention include the antibodies disclosed in the patent applications WO 2009/058797, WO 08/097,461 and WO 2009/044284, for example.

The adsorbent includes ligands covalently bonded to a solid phase. The solid phase may be based on organic or inorganic material, but the solid phase is preferably made of organic material. The solid phase is ideally compatible with whole blood. A whole blood-compatible adsorbent allows adsorption in an extracorporeal circulation without separation into blood plasma and cell suspension. In this way a medical device having exclusively a primary circulation may be used, in contrast with the more complex alternative also disclosed, namely a medical device having a secondary circulation in addition to the primary circulation.

Whole blood adsorbents consist of particles which are so large that they form interspaces in which the blood cells can move. Furthermore, the particles have pores which lead to an internal surface. These pores are of a sufficient size so that even macromolecules can penetrate into them. However, the pores are selected to be so small that penetration of blood cells is prevented. The blood cells thus have contact only with the external surface of the particles. Furthermore, these particles must be as spherical and unaggregated as possible according to EP 0 424 698 to have a "smooth" as well as inert exterior, so that platelets can slip over them.

The depletion unit advantageously consists of a preferably rigid housing filled with the particulate adsorbent. The particles are held in the interior of the housing by fine-mesh screens at the inlet and outlet of the blood or blood plasma, thereby preventing a transfer of these particles to the patient's blood.

The porous organic carrier material of the inventive adsorbent has an average pore size and/or an average pore diameter with a value of ≤1.5 µm, preferably ≤1.0 µm, max. 50% of the pore volume being present in pores with a pore size of >1.5 µm. The maximum average pore size of 1.5 µm is determined by the size of the smallest blood cells, having a diameter of approximately 2 µm. At a maximum average pore size, as defined according to the present invention, it is ensured that essentially no blood cells can penetrate into the pores. On the other hand, the pores should be large enough to be able to accommodate the substances to be depleted. In the case of hepcidin, the pores should be able to accommodate not only the small hepcidin but also the much larger hepcidin-binding alpha-2-macroglobulin. The pores must thus be suitable for accommodating macromolecules with a molecular weight of 750 kDa. For this reason, the pores preferably have an average size of at least 0.05 µm, preferably a size of at least 0.1 µm and especially preferably a size of at least 0.3 µm.

According to the invention, the average pore size can be determined by mercury intrusion (mercury intrusion porosimetry) according to DIN 66 133. This method is based on measurement of the mercury volume forced into a porous solid as a function of the applied pressure. A non-wetting liquid such as mercury penetrates into a porous system only under pressure. The pressure to be applied is inversely proportional to the inside diameter of the pore openings. Pores into which mercury can penetrate at the pressure applied are detected by this method. For cylindrical pores, the relationship between the pore radius rp and the pressure p is expressed by the Washburn equation, where s is the surface tension of mercury [N/m] and J is the contact angle of mercury on the sample, measured through the liquid phase. In deviation from DIN Standard 66 133, the fixed value 141.3° is used for the contact angle, and the interparticle volumes are not included in the determination of the average pore size.

Furthermore, the adsorbent particles preferably have a particle size of 50 µm to 500 µm, more preferably from 100 µm to 300 µm. For use in an extracorporeal circulation with whole blood, the adsorbent particles should have a particle size of at least 50 µm because the largest blood cells present in whole blood have a diameter of 20 µm. The screen which retains the adsorbent must therefore have a mesh of at least 25 µm, preferably at least 40 µm, in order for all the blood cells to pass through. Furthermore, the interspace between the particles in columns packed with adsorbent particles 50 µm in size or more is sufficient for the passage of blood cells. In selecting the screen material, it is also important to be sure that the mesh size is always smaller than the diameter of the smallest adsorber particles.

The inventive adsorbent preferably comprises a porous particulate carrier material. According to this embodiment, carrier materials that are suitable include, for example, carbohydrates, sepharose or organic carrier materials such as copolymers of acrylates or methacrylates and polyamides. The carrier materials preferably consist of copolymers derived from (meth)acrylic acid esters and/or (meth)acrylamides, which preferably have epoxy groups. The term "(meth)acryl" is understood to include the corresponding acryl compounds as well as methacryl compounds.

The ligand may be covalently bonded to the carrier material with any conventional method known in the state of the art. Conventional methods include, for example, bonds by way of an epoxy reaction, an Ni-base reaction, a condensation reaction with a carbodiimide, a reaction with ester activation and crosslinking reactions with a glutaraldehyde. In addition to the conventional methods mentioned above for immobilizing ligands on solid phases, there are also various suppliers of solid-phase systems (e.g., Eupergit, Toyopearl) who stipulate a certain bonding to the solid phase which is predetermined by the properties of the solid phase and/or is especially advantageous.

EXAMPLE 1

A purified fraction of monoclonal hepcidin-25 binding antibody of the IgG type was dissolved at a pH of 7.5 in PBS in a concentration of 3 mg/mL. To 5 mL of this solution was added 1 g oxirane-acrylic beads (Eupergit C, Röhm GmbH & Co. KG). The suspension was stored in the dark for 48 hours at room temperature and then diluted with an additional 3 mL PBS. After separating the beads from the supernatant, a concentration of less than 50 µg/mL was found in the supernatant. The resulting adsorbent was washed with PBS at a pH of 7.5. The adsorbent was stirred for 12 hours with 10 mL of a 10% aqueous ethanolamine solution at a pH of 9 and a temperature of 4° C. to fully react the remaining oxirane groups. The adsorbent was then washed again with PBS at a pH of 7.5.

The invention claimed is:

1. A medical device, useful for extracorporeally depleting unwanted substances from the blood of a patient, comprising
   a) a first line for carrying blood connectable to the patient,
   b) a second line for carrying blood connectable to the patient,
   c) a depletion unit connected with a liquid-tight seal to the first blood carrying line,
   d) an adsorbent contained in the depletion unit and containing
      i) a matrix of essentially spherical, unaggregated porous particles having pores with an average pore size of less than 1.5 µm and more than 0.1 µm and
      ii) a ligand covalently bonded to the matrix, which ligand binds to hepcidin with an affinity having a dissociation constant KD of less than 200 nM,
   e) a hemodialyzer,
   f) a controllable body fluid delivery device arranged in one or each of the first line and the second line for controlling flow of body fluid through the line and the depletion unit such that the first line continuously supplies body fluid from the patient to the depletion unit and the second line continuously supplies body fluid to the patient.

2. The device according to claim 1, additionally comprising a filter having an unfiltered side and a filtered side, such that
   the unfiltered side is separated from the filtered side by at least one filter material,
   a fluid supply inlet of the unfiltered side is connected to a third line connectable to the patient,
   a fluid removal outlet of the unfiltered side is connected to a fourth line connectable to the patient,
   a fluid removal outlet of the filtered side is connected to the first line, and
   a fluid supply inlet of the filtered side is connected to the second line.

3. The device according to claim 1, wherein the ligand is a monoclonal antibody or an antibody fragment.

4. The device according to claim 1, wherein the ligand is a humanized monoclonal antibody or antibody fragment.

5. The device according to claim 1, wherein the ligand is a peptide having at least 80 percent homology with the peptide sequence of the binding region of the alpha-2-macroglobulin.

6. The device according to claim 1, wherein the matrix is composed of an organic polymer.

* * * * *